(12) United States Patent
Proksa et al.

(10) Patent No.: US 10,441,230 B2
(45) Date of Patent: Oct. 15, 2019

(54) PROJECTION DATA ACQUISITION APPARATUS

(71) Applicant: KONINKLIJKE PHILIPS N.V., Eindhoven (NL)

(72) Inventors: Roland Proksa, Neu Wulmstorf (DE); Michael Grass, Buchholz In der Nordheide (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 114 days.

(21) Appl. No.: 15/325,158

(22) PCT Filed: Jul. 13, 2015

(86) PCT No.: PCT/EP2015/065993
§ 371 (c)(1),
(2) Date: Jan. 10, 2017

(87) PCT Pub. No.: WO2016/008856
PCT Pub. Date: Jan. 21, 2016

(65) Prior Publication Data
US 2017/0172525 A1    Jun. 22, 2017

(30) Foreign Application Priority Data
Jul. 15, 2014 (EP) .................... 14176988

(51) Int. Cl.
*A61B 6/00* (2006.01)
*A61B 6/06* (2006.01)
(Continued)

(52) U.S. Cl.
CPC ............... *A61B 6/06* (2013.01); *A61B 6/032* (2013.01); *A61B 6/405* (2013.01); *A61B 6/4429* (2013.01);
(Continued)

(58) Field of Classification Search
CPC .......... A61B 6/032; A61B 6/06; A61B 6/405; A61B 6/4429; A61B 6/5282; A61B 6/542; G01N 23/046
See application file for complete search history.

(56) References Cited

U.S. PATENT DOCUMENTS

| 4,995,066 A * | 2/1991 | Harding | A61B 6/06 378/146 |
| 6,744,845 B2 * | 6/2004 | Harding | A61B 6/032 378/16 |

(Continued)

FOREIGN PATENT DOCUMENTS

| EP | 0236790 | 9/1987 |
| JP | 52125291 | 10/1977 |

(Continued)

OTHER PUBLICATIONS

Zhu, et al., "Scatter Correction Method for X-Ray CT Using Primary Modulation: Theory and Preliminary Results", IEEE Transactions on Medical Imaging, vol. 25, No. 12, Dec. 2006.

(Continued)

*Primary Examiner* — Dani Fox
(74) *Attorney, Agent, or Firm* — Larry Liberchuk (57) ABSTRACT

The invention relates to a projection data acquisition apparatus (31) for acquiring projection data. The projection data acquisition apparatus comprises a radiation device (32) for generating a pulsed radiation beam (4) for traversing an object and a detection device (6) for generating projection data being indicative of the pulsed radiation beam (4) at different acquisition positions, wherein the radiation device (32) is adapted to generate the pulsed radiation beam (4) such that at different acquisition positions the pulsed radiation beam (4) has different shapes, i.e. is differently blocked and/or attenuated. Thus, not the complete radiation providable by the radiation device is used at each acquisition (Continued)

position, but at least at some acquisition positions only a smaller pulsed radiation beam is used. This can lead to less scattered radiation and hence to improved projection data and an improved computed tomography image, which may be reconstructed based on the acquired projection data.

17 Claims, 6 Drawing Sheets

(51) Int. Cl.
    *A61B 6/03*     (2006.01)
    *G01N 23/046*     (2018.01)

(52) U.S. Cl.
    CPC ............ *A61B 6/5282* (2013.01); *A61B 6/542* (2013.01); *G01N 23/046* (2013.01)

(56) References Cited

U.S. PATENT DOCUMENTS

| | | | |
|---|---|---|---|
| 8,144,829 B2 | 3/2012 | Zhu | |
| 2006/0008048 A1 | 1/2006 | Katada | |
| 2007/0104320 A1 | 5/2007 | Arenson | |
| 2007/0172031 A1 | 7/2007 | Cason | |
| 2008/0080663 A1* | 4/2008 | Haerer | G06T 5/002 378/7 |
| 2008/0232543 A1* | 9/2008 | Pasini | A61B 6/032 378/16 |
| 2009/0283682 A1 | 11/2009 | Star-Lack | |
| 2012/0121063 A1* | 5/2012 | Proksa | A61B 6/032 378/16 |
| 2012/0215095 A1 | 8/2012 | Av-Shalom | |
| 2013/0003929 A1 | 1/2013 | McNabb | |
| 2013/0279783 A1 | 10/2013 | Schmitt | |
| 2014/0086380 A1 | 3/2014 | Song | |
| 2015/0305696 A1* | 10/2015 | Yamakawa | A61B 6/14 378/19 |

FOREIGN PATENT DOCUMENTS

| | | |
|---|---|---|
| WO | 01/60236 | 8/2001 |
| WO | 2007/120744 | 10/2007 |
| WO | 01/37287 | 5/2011 |

OTHER PUBLICATIONS

Cho, et al., "Feasibility study on many-view undersampling technique for low-dose computed tomography", Optical Engineering, Aug. 2012/vol. 51(8).

* cited by examiner

PROJECTION DATA ACQUISITION APPARATUS

CROSS REFERENCE TO RELATED APPLICATIONS

This application is the U.S. National Phase application under 35 U.S.C. § 371 of International Application No. PCT/EP2015/065993, filed Jul. 13, 2015, published as WO 2016/008856 on Jan. 21, 2016, which claims the benefit of European Patent Application Number 14176988.5 filed Jul. 15, 2014. These applications are hereby incorporated by reference herein.

FIELD OF THE INVENTION

The invention relates to a projection data acquisition apparatus, method and computer program for acquiring projection data. The invention relates further to a collimator, which may be used by the projection data acquisition apparatus, a computed tomography system comprising the projection data acquisition apparatus and a corresponding computed tomography method and computer program.

BACKGROUND OF THE INVENTION

A computed tomography system comprises a radiation device for generating a radiation beam for traversing an object, a detection device for generating projection data being indicative of the radiation after having traversed the object, a moving unit for moving the radiation device and the object relative to each other, in order to generate the projection data at different acquisition positions of the radiation device relative to the object, and a reconstruction unit for reconstructing a computed tomography image of the object based on the generated projection data. In order to reduce the radiation dose applied to the object, the object may not be irradiated at all possible acquisition positions along an acquisition trajectory, along which the radiation device is moved relative to the object, but only at some of these acquisition positions. However, the computed tomography image, which is reconstructed based on these sparsely sampled projection data, may have a reduced image quality.

SUMMARY OF THE INVENTION

It is an object of the present invention to provide a projection data acquisition apparatus, method and computer program for acquiring projection data, which allow for a sampling of the projection data such that the quality of a computed tomography image, which is reconstructed based on the sampled projection data, can be improved. It is a further object of the present invention to provide a collimator, which may be used by the projection data acquisition apparatus, a computed tomography system comprising the projection data acquisition apparatus and a corresponding computed tomography method and computer program.

In a first aspect of the present invention a projection data acquisition apparatus for acquiring projection data is presented, wherein the projection data acquisition apparatus comprises:

a radiation device for generating a pulsed radiation beam for traversing an object,
a detection device for generating projection data being indicative of the pulsed radiation beam after having traversed the object,
a moving unit for moving the radiation device and the object relative to each other, in order to generate the projection data at different acquisition positions of the radiation device relative to the object,
wherein the radiation device is adapted to generate the pulsed radiation beam such that at different acquisition positions the pulsed radiation beam has different shapes, and wherein the radiation device comprises a radiation source for generating a radiation beam and a collimator for partially blocking and/or attenuating the radiation beam, in order to generate the pulsed radiation beam such that at different acquisition positions the pulsed radiation beam has different shapes, wherein the collimator is adapted to partially block the radiation beam such that a shadowed region and a non-shadowed region are generated on the detection device, wherein the detection device is adapted to generate the projection data based on the pulsed radiation beam directed onto the non-shadowed region and to generate scatter data based on radiation, which has been scattered onto the shadowed region, wherein the projection data acquisition apparatus further comprises a correction unit for correcting the generated projection data based on the scatter data. Since at the different acquisition positions the pulsed radiation beam has different shapes, i.e. since at different acquisition positions the pulsed radiation beam may be differently blocked or attenuated, not the complete radiation providable by the radiation device is used at each acquisition position, but at least at some acquisition positions only a smaller pulsed radiation beam is used. Using these smaller pulsed radiation beams at least at certain acquisition positions leads to less scattered radiation, wherein generally scattered radiation does not only generate image artifacts, but also increases the noise. Thus, by using the smaller pulsed radiation beams at least at certain acquisition positions image artifacts can be reduced and the signal-to-noise ratio can be increased, thereby improving the quality of a computed tomography image, which may be reconstructed based on the acquired projection data. The radiation device comprises a radiation source for generating a radiation beam and a collimator for partially blocking and/or attenuating the radiation beam, in order to generate the pulsed radiation beam such that at different acquisition positions the pulsed radiation beam has different shapes. The shape of the pulsed radiation beam may be different for two or more acquisition positions, at which a pulsed radiation beam is generated. The radiation source may be adapted to generate a pulsed radiation beam, wherein the collimator may be adapted to partially block or attenuate the pulsed radiation beam for generating the pulsed radiation beam such that at different acquisition positions the pulsed radiation beam has different shapes. The radiation source may be a grid switching x-ray source. A grid switching x-ray source allows for a very fast and temporally accurate generation of the pulsed radiation beam, which can lead to a further improved quality of the finally reconstructed computed tomography image. However, in an embodiment the radiation source may also provide a continuous radiation beam, wherein the continuous radiation beam may be completely blocked at some positions along an acquisition trajectory, along which the radiation source moves relative to the object, and partly and differently blocked at acquisition positions along the acquisition trajectory, at which projection data should be acquired, in order to generate the pulsed radiation beam such that at different acquisition positions the pulsed radiation beam has different shapes.

The collimator is adapted to partially block the radiation beam such that a shadowed region and a non-shadowed region are generated on the detection device, wherein the detection device is adapted to generate the projection data based on the pulsed radiation beam directed onto the non-shadowed region and to generate scatter data based on radiation, which has been scattered onto the shadowed region, wherein the projection data acquisition apparatus further comprises a correction unit for correcting the generated projection data based on the scatter data. This can lead to a further improved quality of the projection data and hence of a computed tomography image which may be reconstructed based on the projection data.

The collimator may comprise a rotatable cylinder with several openings, wherein the collimator may be adapted to rotate the cylinder such that the openings are arranged at different rotational position relative to the radiation source at different acquisition positions, in order to generate the pulsed radiation beam such that at the different acquisition positions the pulsed radiation beam has different shapes. In particular, the openings of the cylinder preferentially include first openings arranged at a first position along a longitudinal axis of the cylinder and second openings arranged at a second position along the longitudinal axis of the cylinder, wherein the first openings and the second openings have a circumferential offset relative to each other. Using this collimator allows for an accurate and fast different shaping at the different acquisition positions by rotating the cylinder such that the openings are arranged at different positions relative to the radiation source at the different acquisition positions.

The projection data acquisition apparatus may further comprise a radiation dose constraints providing unit for providing spatial radiation dose constraints defining upper radiation dose limits for different spatial regions within the object, wherein the radiation device, the detection device and the moving unit are adapted to generate the projection data such that the provided spatial radiation dose constraints are fulfilled. Thus, the radiation device, the detector and the moving unit may be adapted to generate the projection data such that the radiation dose applied to the object is not too high, especially, as high as possible without adversely affecting the object, which can lead to an improved signal-to-noise ratio of the acquired projection data and hence finally to a further improved computed tomography image, which may be reconstructed based on the acquired projection data. The constraints may be different for different parts of the object such that the radiation doses applied to the respective parts of the object can be specifically adapted to the respective parts. However, the partial radiation dose constraints can also define a same upper radiation dose limit for the entire object.

It is further preferred that the radiation device is adapted such that the pulse duration of the pulsed radiation beam is different at different acquisition positions. By varying the pulse duration of the pulsed radiation beam for different acquisition positions the radiation dose applied at the different acquisition positions can be varied. This variation of the pulse duration can be used, for instance, to generate the projection data such that the spatial radiation dose constraints, which may be provided by the radiation dose constraints providing unit, are fulfilled.

In a preferred embodiment the moving unit is adapted to move the radiation device relative to the object along an acquisition trajectory during the acquisition of the projection data, wherein the radiation device and the detection device are adapted to allow an acquisition of projection data at a group of different acquisition positions along the acquisition trajectory and to actually generate the pulsed radiation beam and detect the pulsed radiation beam, after having traversed the object, only at a subgroup of the group of different acquisition positions. Thus, preferentially the projection data are sparsely sampled, thereby reducing the radiation dose applied to the object.

In a further aspect of the present invention a use of a collimator for collimating radiation generated by a radiation source of a projection data acquisition apparatus as defined in claim 1 is presented, wherein the collimator comprises a rotatable cylinder with several openings which include first openings arranged at a first position along a longitudinal axis of the cylinder and second openings arranged at a second position along the longitudinal axis of the cylinder, wherein the first openings and the second openings have a circumferential offset relative to each other.

In a further aspect of the present invention a computed tomography system for generating a computed tomography image of an object is presented, wherein the computed tomography system comprises:
  a projection data acquisition apparatus for acquiring projection data of the object as defined in claim 1,
  a reconstruction unit for reconstructing a computed tomography image of the object based on the acquired projection data.

In another aspect of the present invention a projection data acquisition method for acquiring projection data is presented, wherein the projection data acquisition method comprises:
  generating a pulsed radiation beam for traversing an object by a radiation device,
  generating projection data being indicative of the pulsed radiation beam after having traversed the object by a detection device,
  moving the radiation device and the object relative to each other by a moving unit, in order to generate the projection data at different acquisition positions of the radiation device relative to the object,
  wherein the radiation device generates the pulsed radiation beam such that at different acquisition positions the pulsed radiation beam has different shapes,
  wherein the collimator partially blocks the radiation beam such that a shadowed region and a non-shadowed region are generated on the detection device, wherein the detection device generates the projection data based on the pulsed radiation beam directed onto the non-shadowed region and to generate scatter data based on radiation, which has been scattered onto the shadowed region, wherein the generated projection data are corrected based on the scatter data by using a correction unit.

In another aspect of the present invention a computed tomography method for generating a computed tomography image of an object is presented, wherein the computed tomography method comprises:
  acquiring projection data of the object as defined in claim 12 by a projection data acquisition apparatus as defined in claim 1,
  reconstructing a computed tomography image of the object based on the acquired projection data by a reconstruction unit.

In a further aspect of the present invention a computer program for acquiring projection data is presented, wherein the computer program comprises program code means for causing a projection data acquisition apparatus as defined in claim 1 to carry out the steps of the projection data acquisition method as defined in claim 10, when the computer program is run on a computer controlling the projection data acquisition apparatus.

In a further aspect of the present invention a computer program for generating a computed tomography image of an object is presented, wherein the computer program comprises program code means for causing a computed tomography system as defined in claim 9 to carry out the steps of the computed tomography method as defined in claim 11, when the computer program is run on a computer controlling the computed tomography system.

It shall be understood that the projection data acquisition apparatus of claim 1, the computed tomography system of claim 9, the projection data acquisition method of claim 10, the computed tomography method of claim 11, the computer program for acquiring projection data of claim 12, and the computer program for generating a computed tomography image of claim 13 have similar and/or identical preferred embodiments, in particular, as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
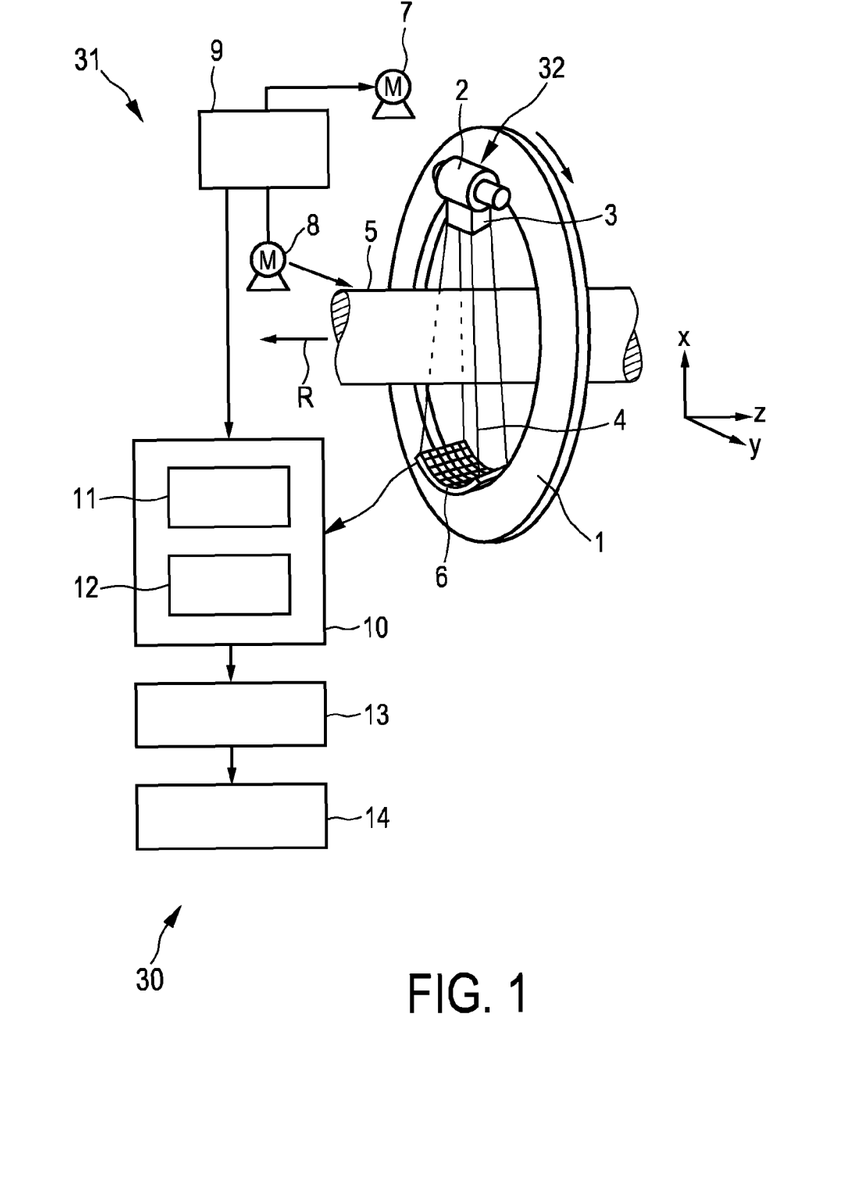
FIG. 1 shows schematically and exemplarily an embodiment of a computed tomography system for generating a computed tomography image of an object.

FIG. 1 shows schematically and exemplarily an embodiment of a computed tomography system for generating a computed tomography image of an object. The computed tomography system 30 includes a gantry 1 which is capable of rotation about a rotational axis R which extends parallel to a z axis. A radiation device 32 is mounted on the gantry 1. The radiation device 32 comprises a radiation source 2 for generating a pulsed radiation beam 4 and a collimator 3 for shaping the generated pulsed radiation beam 4. In particular, the collimator 3 is adapted to partially block the pulsed radiation beam 4 for shaping the pulsed radiation beam 4. The radiation source 2 is preferentially a grid switching x-ray source.

The radiation 4 traverses an object (not shown), such as a person, in an examination zone 5 being, in this embodiment, cylindrical. After having traversed the examination zone 5 and thus the object within the examination zone 5 the radiation beam 4 is incident on a detection device 6 which comprises a two-dimensional detection surface. Also the detection device 6 is mounted on the gantry 1.

The computed tomography system 30 further comprises two motors 7, 8, wherein the gantry 1 is driven at a preferably constant but adjustable angular speed by the motor 7. The motor 8 is provided for displacing the object, which is preferentially arranged on a support means like a table, within the examination zone 5 parallel to the direction of the rotational axis R or the z axis. These motors 7, 8 are controlled by a control unit 9, for instance, such that the radiation device 32 and the object are moved relatively to each other along a helical acquisition trajectory. However, it is also possible that the object is not moved, but that only the radiation device 32 is rotated, i.e. that the radiation device 32 moves along a circular trajectory relative to the object. Since the motors 7, 8 move the radiation device 32 and the object relative to each other, they can be regarded as forming a moving unit for moving the radiation device 32 and the object relative to each other.

During the relative movement of the radiation device 32 and the object the detection device 6 generates projection data depending on the radiation incident on the detection surface of the detection device 6, wherein due to the relative movement these projection data are generated at different acquisition positions of the radiation device 32 relative to the object. The radiation device 32 is adapted to generate the pulsed radiation beam 4 such that at different acquisition positions the pulsed radiation beam 4 has different shapes, i.e. in this embodiment the collimator 3 is adapted to differently block the pulsed radiation beam 4 at the different acquisition positions. In particular, the motors 7, 8 are adapted to move the radiation device 32 relative to the object along an acquisition trajectory during the acquisition of the projection data, wherein the radiation device 32 and the detection device 6 are adapted to generally allow for an acquisition of protection data at a group of different acquisition positions and to actually generate the pulsed radiation beam 4 and detect the pulsed radiation beam 4, after having traversed the object, only at a subgroup of the group of different acquisition positions. Thus, the radiation device 32 and the detection device 6 acquire projection data not at all possible acquisition positions along the acquisition trajectory, but only at few acquisition positions along the acquisition trajectory, in order to only sparsely sample the projection data.

The computed tomography system 30 further comprises a radiation dose constraints providing unit 11 for providing spatial radiation dose constraints defining upper radiation dose limits for different spatial regions within the object, wherein the radiation device 32, the detection device 6 and the motors 7, 8 are adapted to generate the projection data such that the provided spatial radiation dose constraints are fulfilled. The radiation source 2 is preferentially adapted such that the pulse duration of the pulsed radiation beam 4 can also be varied for different acquisition positions, wherein this pulse duration variation can be used for generating the projection data such that the provided spatial radiation dose constraints are fulfilled. Thus, a virtual dynamic bowtie filtration can be provided, wherein the x-ray flux pulses radiate different areas of the object and wherein for each of these areas the radiation dose can be adapted by blocking the pulsed radiation beam accordingly and optionally also by modulating the pulse time for each pulse, for instance, by modulating the duty cycle of the grid switch, if the radiation source is a grid switching x-ray source. This may allow for a spatial control of the radiation, which is similar to the spatial control of radiation provided by a dynamic bowtie filter.

Since the collimator 3 is adapted to partially block the pulsed radiation beam 4 at least at some acquisition positions, a shadowed region and a non-shadowed region are generated on the detection device 6 when illuminated by the pulsed radiation beam 4 at the respective acquisition position. The detection device 6 is adapted to generate the projection data based on the pulsed radiation beam 4 directed onto the non-shadowed region and to generate scatter data based on radiation, which has been scattered onto the shadowed region, wherein the computed tomography system 30 further comprises a correction unit 12 for correcting the generated projection data based on the scatter data. Thus, detector readings of pixels in a shadowed detector area are used to estimate and correct for the scatter of the non-shadowed detector area. For performing this correction the correction unit 12 can be adapted to use known scatter correction algorithms which are based on the assumption that the scattered radiation, i.e. the scatter data, has only low spatial frequency components, wherein these low spatial frequency components are estimated based on the scatter data and used to correct the projection data. For instance, the scatter correction algorithm disclosed in the article "Scatter Correction Method for X-Ray CT Using Primary Modulation: Theory and Preliminary Results" by L. Zhu et al., IEEE Transactions on Medical Imaging, volume 25, number 12, pages 1573 to 1587 (2006), which is herewith incorporated by reference, or another known scatter correction algorithm can be adapted for correcting the projection data.

Figure 2:
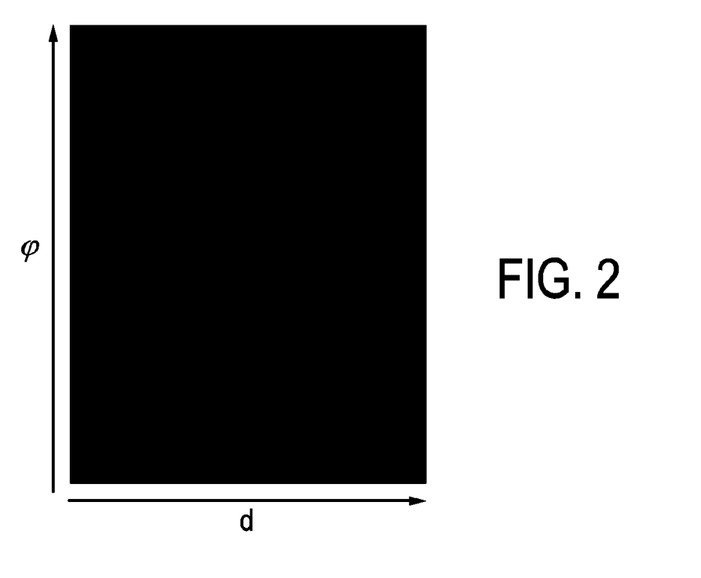
FIG. 2 shows a graph exemplarily illustrating a full sampling projection data acquisition technique.
Figure 3:
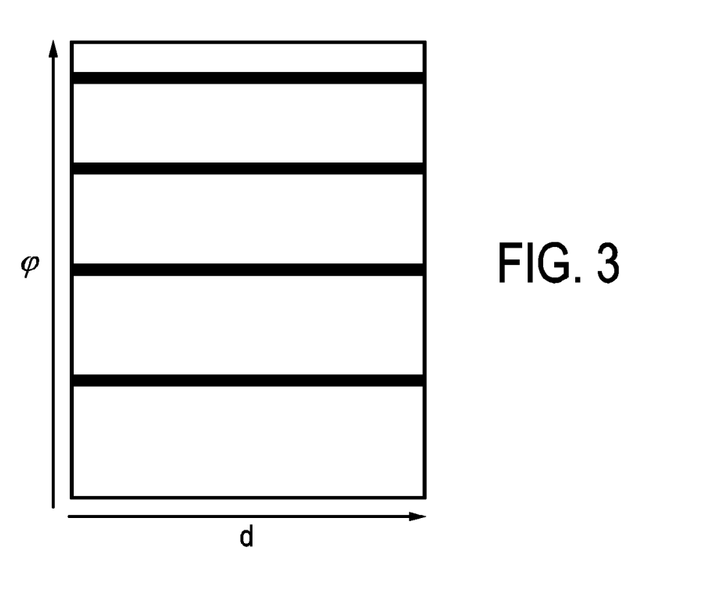
FIG. 3 shows a graph exemplarily illustrating a temporal subsampling projection data acquisition technique.
Figure 4:
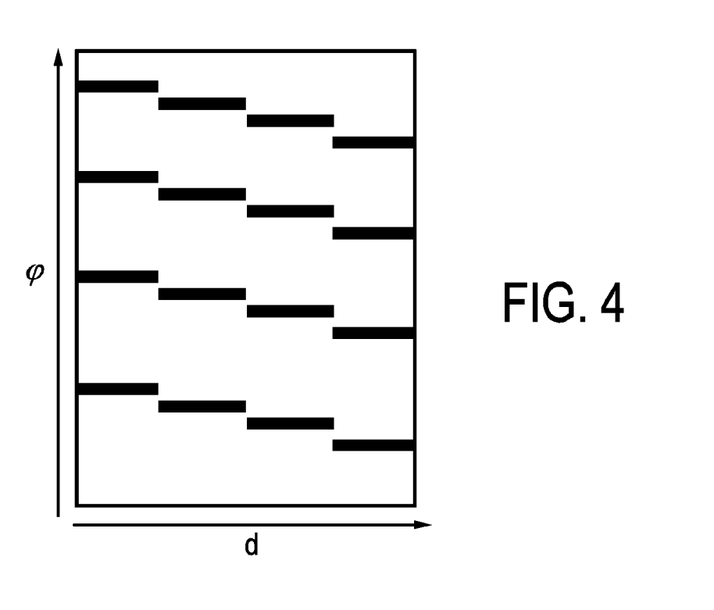
FIG. 4 shows a graph exemplarily illustrating a combined temporal and spatial subsampling projection data acquisition technique.

FIG. 4 schematically and exemplarily illustrates the acquisition of the projection data performed by the computed tomography system 30 in comparison to other acquisitions of projection data, which are schematically and exemplarily illustrated in FIGS. 2 and 3 and which may be performed by other computed tomography systems.

FIGS. 2 to 4 show three graphs respectively indicating which detection elements d of a row of detection elements of the detection device 6 are illuminated by the pulsed radiation beam at which acquisition positions indicated by the angle φ. FIG. 2 illustrates a non-pulsed acquisition of projection data, i.e. for each acquisition position φ all detection elements d of the respective detection row are irradiated. FIG. 3 illustrates a sparse sampling without differently blocking the pulsed radiation beam at different acquisition positions φ, i.e. at the acquisition positions φ, at which a pulsed radiation beam is generated, always the same detector elements of the respective detector row are irradiated by the pulsed radiation beam. In contrast, as illustrated in FIG. 4, the computed tomography system 30 described above with reference to FIG. 1 is adapted to shape the pulsed radiation beam at different acquisition positions φ differently by differently blocking the pulsed radiation beam. Thus, FIG. 2 illustrates a full sampling, FIG. 3 illustrates an angular, which may also be regarded as being a temporal, subsampling and FIG. 4 illustrates a combined angular, i.e. temporal, and spatial subsampling as performed by the computed tomography system 30 described above with reference to FIG. 1.

The radiation dose constraints providing unit 11 and the correction unit 12 can be integrated in a single unit 10. Moreover, the radiation dose constraints providing unit 11 can comprise a storing unit, in which the radiation dose constraints are stored already and from which the radiation dose constraints can be retrieved for providing the same. The radiation dose constraints providing unit 11 can also comprise a graphical user interface for allowing a user to input desired spatial radiation dose constraints. Both units may also be controlled by the control unit 9. However, they may also be controlled by another controller. Furthermore, the radiation device 32, the detection device 6, the gantry 1, the motors 7, 8, the control unit 9, the radiation dose constraints providing unit 11 and the correction unit 12 are all used for providing projection data. These components can therefore be regarded as being components of a projection data acquisition apparatus 31.

The computed tomography system 30 further comprises a reconstruction unit 13 for reconstructing a computed tomography image of the object within the examination zone 5 based on the acquired projection data. In particular, the reconstruction unit 13 is adapted to use an iterative reconstruction technique for reconstructing the computed tomography image based on the acquired projection data. Also the reconstruction unit 13 may be controlled by the control unit 9. However, it may also be controlled by another controller. Moreover, the computed tomography system 30 comprises a display 14 for displaying at least the reconstructed computed tomography image.

Figure 5:
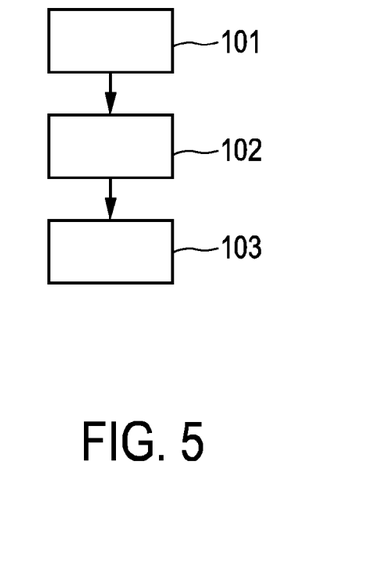
FIG. 5 shows a flowchart exemplarily illustrating an embodiment of a computed tomography method for generating a computed tomography image of an object.

In the following an embodiment of a computed tomography method for generating a computed tomography image of an object will exemplarily be described with reference to a flowchart shown in FIG. 5.

In step 101 projection data are acquired. In particular, a) the radiation device 32 and the object are moved relative to each other by using the gantry 1, the support means on which the object is lying and the motors 7, 8, b) a pulsed radiation beam for traversing the object is generated by the radiation device 32, and c) projection data being indicative of the pulsed radiation beam 4 after having traversed the object are generated by the detection device 6, in order to generate the projection data at different acquisition positions of the radiation device 32 relative to the object. A sparse sampling is preferentially performed, wherein the projection data are not acquired at all possible acquisition positions along an acquisition trajectory, but only at some of these acquisition positions. Moreover, during the acquisition of the projection data the radiation device 32 generates the pulsed radiation beam 4 such that at different acquisition positions the pulsed radiation beam 4 has different shapes, especially is differently blocked by using the collimator 3. Also the pulse duration of the pulsed radiation beam may be varied for different acquisition positions. These substeps performed in step 101, in order to acquire the projection data, can be regarded as being steps of a projection data acquisition method for acquiring projection data.

In step 102 the reconstruction unit 13 reconstructs a computed tomography image based on the projection data acquired in step 101. Preferentially, the reconstruction unit 13 iteratively constructs the computed tomography image based on the acquired projection data. The reconstructed computed tomography image is then shown on the display 14 in step 103.

The computed tomography system described above with reference to FIG. 1 can be regarded as being a high x-ray flux and large area detector computed tomography system, which because of the high x-ray flux and the large area detector allows for ultra-fast imaging, especially if the detection surface of the detection device is completely irradiated as schematically and exemplarily indicated in FIG. 1. However, some imaging applications may not need this ultra-fast imaging capability. The computed tomography system allows therefore for a sparse-angular sampling, i.e. instead of a constantly radiating beam short x-ray pulses are used for imaging, yielding a reduced number of projections per gantry rotation. These short x-ray pulses are preferentially generated with a grid switching x-ray tube. Moreover, the computed tomography system is adapted to extend the sparse-angular sampling preferentially using a grid switching x-ray source to a partial beam sampling, i.e. in addition to the temporal beam blanking the x-ray beam is partially blocked, wherein this partial blocking is achieved by using a dynamic collimator which generates different beam shapes during the scan. The dynamic collimator may comprise, for instance, two or more movable leafs, which can block the radiation, wherein these leafs can be moved to different positions at different acquisition positions, in order to differently block the pulsed radiation beam at the different acquisition positions. Alternatively, the dynamic collimator may comprise a rotatable hollow cylinder 40 with openings 44 . . . 47 as schematically and exemplarily illustrated in FIG. 6 and a motor (not shown) for rotating the cylinder 40 in the rotational direction indicated by the arrow 43. Also this motor may be controlled by the control unit 9 or by another control unit. Moreover, this motor or a further motor of the collimator may be adapted to move the cylinder 40 into and out of the radiation generated by the radiation source, in order to allow for an operation of the projection data acquisition apparatus in a first mode, in which the detection surface is not influenced by the cylinder 40, especially in which the detection surface is completely illuminated by the radiation emitted by the radiation source, and in a second mode, in which the radiation is influenced by the cylinder 40. The collimator may also be adapted to allow for a manual placing of the cylinder 40 into and out of the radiation generated by the radiation source.

Figure 6:
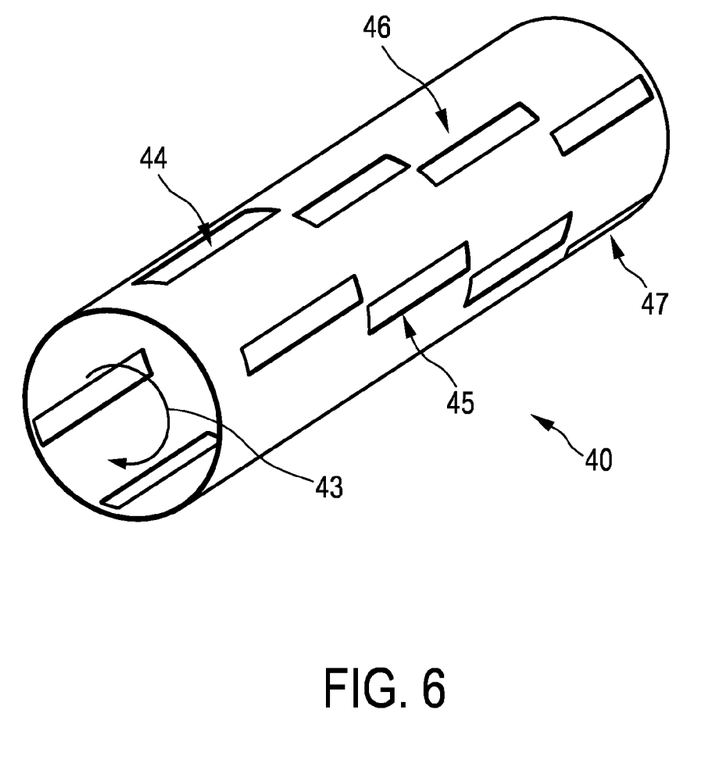
FIG. 6 shows schematically and exemplarily a rotatable cylinder of a collimator of the computed tomography system.

The openings of the cylinder 40 include first openings 44 arranged at a first longitudinal position along a longitudinal axis of the cylinder 40, second openings 45 arranged at a second longitudinal position along the longitudinal axis, third openings 46 arranged at a third longitudinal position along the longitudinal axis and fourth openings 47 arranged at a fourth longitudinal position along the longitudinal axis, wherein the first, second, third and fourth longitudinal positions are different. Moreover, the openings 44 . . . 47, which are arranged at different longitudinal positions, have a circumferential offset relative to each other, i.e. openings, which are arranged at different longitudinal positions, are also arranged at different circumferential positions along the circumference of the cylinder 40. The openings 44 . . . 47 are rectangular, wherein the rectangular openings 44 . . . 47 have a larger dimension in the direction of the longitudinal axis of the cylinder and a smaller dimension in a circumferential direction of the cylinder. Furthermore, in this embodiment the openings at a certain longitudinal position are homogenously, i.e. angularly equidistantly, distributed along the circumference of the cylinder 40. The cylinder 40 is preferentially arranged such that its longitudinal axis is substantially orthogonal to the rotational axis R of the computed tomography system 30.

The cylinder is made of a strong x-ray absorbing material like tungsten. The wall thickness may be in the range of some millimeters, for instance, it may be within a range of 1 to 3 mm. The cylinder is preferentially constructed such that it has a stopping power of about or close to 100 percent. Depending on the geometry of the overall system the cylinder may have a diameter in the range of some centimeters, for instance, within a range of 1 to 4 cm.

Figure 7:
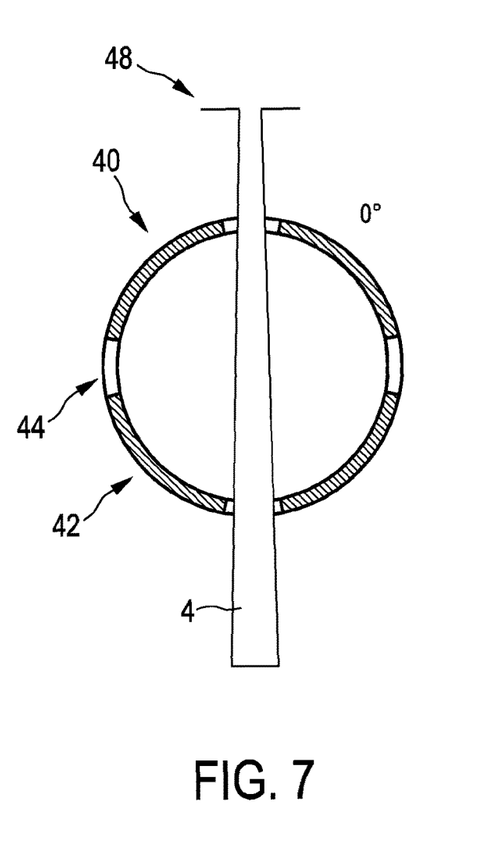
FIG. 7 illustrates schematically and exemplarily a rotational position of the cylinder, in which a part of a radiation beam passes the cylinder.
Figure 8:
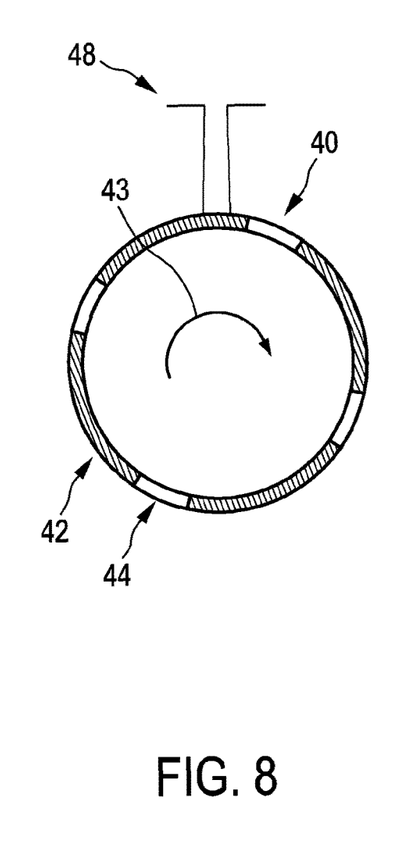
FIG. 8 illustrates schematically and exemplarily a rotational position of the cylinder, at which at least a part of the radiation beam is blocked by the cylinder.

FIG. 7 shows schematically and exemplarily a cross-sectional view of the cylinder 40. In FIG. 7 the cylinder 40 is oriented such that the radiation beam generated by the radiation source 2, which in FIG. 7 is arranged above a further collimating element 48, penetrates the openings 44, i.e. in the orientation shown in FIG. 7 the radiation generated by the radiation source 2 can pass the cylinder 40 and hence the collimator 3. In FIG. 8 a situation is shown, in which the cylinder 40 has been rotated in the direction indicated by the arrow 43 by 22.5 degrees such that the radiation generated by the radiation source 2 is blocked, at least in the shown cross section, by the wall 42 of the cylinder 40.

In addition to the rotatable cylinder the collimator 3 comprise the further collimating element 48, which may be a slit collimating element, for collimating the radiation generated by the radiation source before partly traversing the rotatable cylinder 40 or before being blocked by the rotatable cylinder. The further collimating element 48 preferentially defines the width of the radiation beam in a cross section of the cylinder 40, which is perpendicular to the longitudinal axis of the cylinder 40, such that the radiation beam 4 can pass the cylinder 40 through the respective openings 44 . . . 47 without being further collimated in the width direction, i.e. the width of the radiation beam 4 in the respective cross section is preferentially defined by the further collimating element 48. The collimator 3 may comprise a motor for modifying the slit width and/or the slit width may be manually modifiable, in order to modify the width of the radiation beam in the cross section shown in FIGS. 7 and 8.

The further collimating element 48 can be a standard collimating element which is used in known computed tomography systems for collimating the radiation generated by the radiation source, wherein in contrast to known computed tomography systems in an embodiment the collimator 3 further comprises the rotatable cylinder 40.

The rotation of the cylinder 40 is preferentially synchronized with the acquisition of the projection data such that each radiation pulse generated by the radiation source 2 is collimated with the desired shape. The angular subsampling and the exact acquisition time definition from the radiation source 2 can strongly reduce the speed and accuracy requirements for the dynamic collimator. For instance, if the gantry 1 has a rotation time of 0.5 s and if 100 views are angularly sampled with four beam shapes, i.e. if 400 partial views are present per rotation, the cylinder 40 schematically and exemplarily shown in FIGS. 6 to 8 may rotate with only 1200 rotations per second. A very exact positioning of the collimator 40 may not be required, because a short x-ray pulse is preferentially used and relatively large tolerances for the cylinder angle, i.e. for the rotational position of the cylinder 40, of, for example, about +/−5 degrees, may be allowed without impacting the acquisition of the projection data.

The combination of the temporal and spatial beam blocking has several advantages. For instance, a smaller cone beam generates less scatter radiation, wherein scattered radiation generally does not only generate image artifacts, but also increases the noise. While a mean scatter contribution might be corrected with a scatter correction method, the noise from scattered radiation cannot be subtracted. The fact that less scatter is generated can directly improve the signal-to-noise ratio or it allows for a dose reduction to obtain the same image noise.

Although in above described embodiments the radiation device is adapted to generate a cone beam, which may be partially blocked at certain acquisition positions and wherein this blocking may be different for different acquisition positions, in other embodiments the radiation source may be adapted to generate a fan beam, which may be partially blocked. Although in the above described embodiments the radiation device is adapted to provide a partially blocked radiation beam, in other embodiments the radiation device can be adapted to provide a partially attenuated and optionally also blocked radiation beam, wherein the attenuation of the radiation beam may be different for different acquisition positions. Furthermore, although above it is exemplarily mentioned that the object to be imaged may be a person, in other embodiments the object can also be an animal or a technical object, i.e. a non-living object.

Although in above described embodiments a grid switching x-ray source is used as radiation source, in other embodiments also another radiation source may be used. For instance, another radiation source generating a pulsed radiation beam may be used. Or, a radiation source generating a constant, i.e. continuous, radiation beam may be used, wherein the pulsing behavior may be generated by a collimator like the collimator described above with the cylinder 40, in order to generate differently shaped pulsed radiation beams.

Although in an above described embodiment the rotatable cylinder of the collimator has four openings at a same longitudinal position along the longitudinal axis of the cylinder, in other embodiments the cylinder can comprise more or less openings at a same longitudinal position. Moreover, in an embodiment the number of the openings may not be the same at all longitudinal positions and the openings at a same longitudinal position may not be homogenously, i.e. angularly equidistantly, distributed with respect to the circumference of the cylinder. Furthermore, for some different longitudinal positions the openings may not have a circumferential offset with respect to each other. In addition, although in an above described embodiment the rotatable cylinder of the collimator has openings at four different longitudinal positions, in other embodiments the cylinder can comprise openings at more or less longitudinal positions.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Operations like the correction of the projection data for scatter, the provision of radiation dose constraints, the reconstruction of a computed tomography image, et cetera performed by one or several units or devices can be performed by any other number of units or devices. These operations and/or the control of the computed tomography system in accordance with the computed tomography method and/or the control of the projection data acquisition apparatus in accordance with the projection data acquisition method can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to a projection data acquisition apparatus for acquiring projection data. The projection data acquisition apparatus comprises a radiation device for generating a pulsed radiation beam for traversing an object and a detection device for generating projection data being indicative of the pulsed radiation beam at different acquisition positions, wherein the radiation device is adapted to generate the pulsed radiation beam such that at different acquisition positions the pulsed radiation beam has different shapes, i.e. is differently blocked and/or attenuated. Thus, not the complete radiation providable by the radiation device is used at each acquisition position, but at least at some acquisition positions only a smaller pulsed radiation beam is used. This can lead to less scattered radiation and hence to improved projection data and an improved computed tomography image, which may be reconstructed based on the acquired projection data.

The invention claimed is:

1. A projection data acquisition apparatus for acquiring projection data, the projection data acquisition apparatus comprising:
   a radiation device with a radiation source for generating a pulsed radiation beam for traversing an object,
   a detection device for generating projection data being indicative of the pulsed radiation beam after having traversed the object,
   a moving unit for moving the radiation device and the object relative to each other, in order to generate the projection data at different acquisition positions of the radiation device relative to the object,
   wherein the radiation device is adapted to generate the pulsed radiation beam such that at different acquisition positions the pulsed radiation beam has different shapes, and
   wherein the radiation device comprises a grid switching x-ray source for generating a pulsed radiation beam and a collimator for partially blocking and/or attenuating the pulsed radiation beam,
   wherein the collimator comprises a rotatable cylinder with several openings, and is adapted to rotate the cylinder such that the openings are arranged at different rotational positions relative to the radiation source at the different acquisition positions such that at the different acquisition positions the pulsed radiation beam has different shapes,
   wherein the openings of the cylinder include first openings arranged at a first position along a longitudinal axis of the cylinder and second openings arranged at a second position along the longitudinal axis of the cylinder, wherein the first openings and the second openings have a circumferential offset relative to each other,
   wherein the first and second openings are rectangular, wherein the collimator is adapted to partially block the pulsed radiation beam such that a shadowed region and a non-shadowed region are generated on the detection device, wherein the detection device is adapted to generate the projection data based on the pulsed radiation beam directed onto the non-shadowed region and to generate scatter data based on radiation, which has been scattered onto the shadowed region, wherein the projection data acquisition apparatus further comprises a correction unit for correcting the generated projection data based on the scatter data.

2. The projection data acquisition apparatus as defined in claim 1, wherein the projection data acquisition apparatus further comprises a radiation dose constraints providing unit for providing spatial radiation dose constraints defining upper radiation dose limits for different spatial regions within the object, wherein the radiation device, the detection device and the moving unit are adapted to generate the projection data such that the provided spatial radiation dose constraints are fulfilled.

3. The projection data acquisition apparatus as defined in claim 1, wherein the radiation device is adapted such that a pulse duration of the pulsed radiation beam is different at different acquisition positions.

4. The projection data acquisition apparatus as defined in claim 1, wherein the moving unit is adapted to move the radiation device relative to the object along an acquisition trajectory during the acquisition of the projection data, wherein the radiation device and the detection device are adapted to allow an acquisition of projection data at a group of different acquisition positions along the acquisition trajectory and to actually generate the pulsed radiation beam and detect the pulsed radiation beam-, after having traversed the object, only at a subgroup of the group of different acquisition positions.

5. A computed tomography system for generating a computed tomography image of an object, the computed tomography system comprising:
a projection data acquisition apparatus for acquiring projection data of the object as defined in claim 1,
a reconstruction unit for reconstructing a computed tomography image of the object based on the acquired projection data.

6. A projection data acquisition method for acquiring projection data, the projection data acquisition method comprising:
generating a pulsed radiation beam with a radiation source for traversing an object by a radiation device with a grid switching x-ray source,
generating projection data being indicative of the pulsed radiation beam after having traversed the object by a detection device,
moving the radiation device and the object relative to each other by a moving unit, in order to generate the projection data at different acquisition positions of the radiation device relative to the object,
wherein the radiation device generates the pulsed radiation beam such that at different acquisition positions the pulsed radiation beam has different shapes,
wherein the collimator comprises a rotatable cylinder with several openings, and is adapted to rotate the cylinder such that the openings are arranged at different rotational positions relative to the radiation source at the different acquisition positions such that at the different acquisition positions the pulsed radiation beam has different shapes,
wherein the openings of the cylinder include first openings arranged at a first position along a longitudinal axis of the cylinder and second openings arranged at a second position along the longitudinal axis of the cylinder, wherein the first openings and the second openings have a circumferential offset relative to each other,
wherein the first and second openings are rectangular,
wherein the collimator partially blocks the radiation beam such that a shadowed region and a non-shadowed region are generated on the detection device,
wherein the detection device generates the projection data based on the pulsed radiation beam directed onto the non-shadowed region and to generate scatter data based on radiation, which has been scattered onto the shadowed region,
wherein the generated projection data are corrected based on the scatter data by using a correction unit.

7. A computed tomography method for generating a computed tomography image of an object, the computed tomography method comprising:
acquiring projection data of the object as defined in claim 6 by a projection data acquisition apparatus,
reconstructing a computed tomography image of the object based on the acquired projection data by a reconstruction unit.

8. A computer program for acquiring projection data, the computer program comprising program code means for causing a projection data acquisition apparatus to carry out the steps of the projection data acquisition method as defined in claim 6, when the computer program is run on a computer controlling the projection data acquisition apparatus.

9. A computer program for generating a computed tomography image of an object, the computer program comprising program code means for causing a computed tomography system to carry out the steps of the computed tomography method as defined in claim 7, when the computer program is run on a computer controlling the computed tomography system.

10. The projection data acquisition apparatus as defined in claim 1, further comprising a motor adapted to move the rotatable cylinder into and out of the radiation.

11. The projection data acquisition apparatus as defined in claim 1, wherein the openings include a first set of openings in which each opening is arranged at a first position along a longitudinal axis of the cylinder and angularly offset from each other and a second set of openings in which each opening is arranged at a second different position along a longitudinal axis of the cylinder and angularly offset from each other, and the first and second positions are circumferentially offset from each other.

12. The projection data acquisition apparatus as defined in claim 11, wherein the openings of the first and second sets are rectangularly shaped.

13. The projection data acquisition apparatus as defined in claim 12, wherein each opening has a length along the longitudinal axis and a height in the circumferential direction, and the length is greater than the height.

14. The projection data acquisition apparatus as defined in claim 13, wherein openings at a same position along the longitudinal axis of the cylinder are angularly equidistant with respect to one another.

15. The projection data acquisition apparatus as defined in claim 14, wherein the longitudinal axis is orthogonal to a rotational axis.

16. A non-transitory computer storage medium encoded with computer readable instructions, which, when executed by a processor of a computing system, causes the processor to perform acts of:
- generating a pulsed radiation beam with a radiation source for traversing an object by a radiation device with a grid switching x-ray source;
- generating projection data being indicative of the pulsed radiation beam after having traversed the object by a detection device; and
- moving the radiation device and the object relative to each other by a moving unit, in order to generate the projection data at different acquisition positions of the radiation device relative to the object,
- wherein a collimator partially blocks the radiation beam such that a shadowed region and a non-shadowed region are generated on the detection device,
- wherein the collimator comprises a rotatable cylinder with several openings, and is adapted to rotate the cylinder such that the openings are arranged at different rotational positions relative to the radiation source at the different acquisition positions such that at the different acquisition positions the pulsed radiation beam has different shapes,
- wherein the openings of the cylinder include first openings arranged at a first position along a longitudinal axis of the cylinder and second openings arranged at a second position along the longitudinal axis of the cylinder, wherein the first openings and the second openings have a circumferential offset relative to each other,
- wherein the first and second openings are rectangular,
- wherein the radiation device generates the pulsed radiation beam directed onto the non-shadowed region.

17. The non-transitory computer storage medium of claim 16, wherein the detection device generates scatter data based on radiation, which has been scattered onto the shadowed region, wherein the generated projection data are corrected based on the scatter data by using a correction unit.

* * * * *